(12) United States Patent
Dep et al.

(10) Patent No.: US 9,389,191 B2
(45) Date of Patent: Jul. 12, 2016

(54) CONVEYOR SYSTEM AND MEASURING DEVICE FOR DETERMINING WATER CONTENT OF A CONSTRUCTION MATERIAL

(71) Applicant: Troxler Electronic Laboratories, Inc., Research Triangle Park, NC (US)

(72) Inventors: Wewage Hiran Linus Dep, Research Triangle Park, NC (US); Robert Ernest Troxler, Raleigh, NC (US)

(73) Assignee: Troxler Electronic Laboratories, Inc., Research Triangle Park, NC (US)

( * ) Notice: Subject to any disclaimer, the term of this patent is extended or adjusted under 35 U.S.C. 154(b) by 0 days.

(21) Appl. No.: 13/656,918

(22) Filed: Oct. 22, 2012

(65) Prior Publication Data

US 2014/0110590 A1     Apr. 24, 2014

(51) Int. Cl.
| | |
|---|---|
| *G21K 1/02* | (2006.01) |
| *G01N 23/09* | (2006.01) |
| *G01N 33/38* | (2006.01) |
| *G01N 23/083* | (2006.01) |

(52) U.S. Cl.
CPC .............. *G01N 23/09* (2013.01); *G01N 23/083* (2013.01); *G01N 33/383* (2013.01); *G01N 2223/205* (2013.01); *G01N 2223/613* (2013.01); *G01N 2223/643* (2013.01)

(58) Field of Classification Search
CPC ... G01T 3/00; G01V 23/222; G01V 2223/643
USPC ......................................... 250/363.01–363.1
See application file for complete search history.

(56) References Cited

U.S. PATENT DOCUMENTS

| | | | |
|---|---|---|---|
| 3,213,280 A | | 10/1965 | Burley et al. |
| 3,255,975 A | | 6/1966 | E et al. |
| 3,431,415 A | | 3/1969 | E et al. |
| 3,748,473 A | | 7/1973 | Chen |
| 3,761,712 A | * | 9/1973 | Listerman ..................... 250/388 |
| 3,794,843 A | * | 2/1974 | Chen .......................... 250/359.1 |
| 3,955,087 A | * | 5/1976 | Ashe .......................... 250/360.1 |
| 4,362,939 A | * | 12/1982 | Horiuchi et al. ........... 250/358.1 |
| 4,381,452 A | * | 4/1983 | Jeunehomme ................ 250/392 |
| 4,544,275 A | * | 10/1985 | Hudelmaier .................... 366/30 |

(Continued)

FOREIGN PATENT DOCUMENTS

| | | |
|---|---|---|
| AU | 7192300 A | 5/2001 |
| GB | 898799 A | 6/1962 |

(Continued)

OTHER PUBLICATIONS

Muller, R. H. (1963), Anal. Chem., vol. 35(1), pp. 99A-101A.

(Continued)

*Primary Examiner* — Kiho Kim
(74) *Attorney, Agent, or Firm* — Olive Law Group, PLLC

(57) ABSTRACT

A system is provided. The system includes a conveyor apparatus configured for conveying a material and a water content measurement system positioned about the conveyor apparatus for determining water content in the material. A dimension characteristic measurement system for detecting one or more dimension characteristics of the material is provided and a computer device is configured to manipulate data received from the water content measurement system and the dimension characteristic measurement system to determine a water content of the material.

26 Claims, 6 Drawing Sheets

(56) References Cited

U.S. PATENT DOCUMENTS

| | | | | |
|---|---|---|---|---|
| 4,817,021 | A | * | 3/1989 | Sowerby et al. ............... 702/137 |
| 4,884,288 | A | * | 11/1989 | Sowerby .......................... 378/51 |
| 5,124,552 | A | * | 6/1992 | Anderson ................. 250/339.04 |
| 5,412,217 | A | * | 5/1995 | Miyashita et al. ........ 250/390.05 |
| 8,660,239 | B2 | * | 2/2014 | Radley .......................... 378/146 |
| 2011/0204243 | A1 | * | 8/2011 | Bendahan et al. ............ 250/367 |
| 2011/0222658 | A1 | * | 9/2011 | Radley ............................ 378/62 |

FOREIGN PATENT DOCUMENTS

| | | | |
|---|---|---|---|
| JP | 59114447 A | * 7/1984 | ............ G01N 23/06 |
| SU | 1318896 A1 | 6/1987 | |
| SU | 1556328 A1 | 5/1991 | |

OTHER PUBLICATIONS

Kishkovich, O.; International Search Report and Written Opinion mailed Jan. 10, 2014, for corresponding PCT Patent Application No. PCT/US2013/054245, and references cited therein.

Vermeulen, Clinton et al., Continuous Measurement of Moisture in Nonconducting Materials, IEEE Transactions on Instrumentation and Measurement, vol. 41, No. 6, Dec. 1992.

Notification Concerning Transmittal of International Preliminary Report of Patentability for PCT Application No. PCT/US2013/054245, dated May 7, 2015.

AU Patent Examination Report No. 1 issued May 27, 2016 for AU2013335242.

European Search Report for EP13848148.6 dated May 27, 2016.

* cited by examiner

CONVEYOR SYSTEM AND MEASURING DEVICE FOR DETERMINING WATER CONTENT OF A CONSTRUCTION MATERIAL

TECHNICAL FIELD

This disclosure is related to a conveyor system and measuring system for determining water content of a construction material, and, more particularly, towards a measuring device that determines water content of a concrete and/or aggregate mixture while the mixture travels on a conveyor assembly. The system is high speed and corrects for thickness and density and may do so in real-time.

BACKGROUND

Concrete mixture is made of one or more of sand, aggregate, cement, pozzolans, and other materials and is transported on a conveyor assembly from bins or silos to an area where water and other additives are incorporated into the concrete mixture to homogenize the mixture in preparation for installation and curing. The sand and other aggregates naturally contain a varying amount of water and determining the amount of water already existing in the concrete mixture is important so that the proper amounts of water can be added later during homogenization. It is well known that the water to cement ratio is directly related to the concrete product strength. Improper amounts of water added during the mixing process can impact the curing time, strength, durability, and appearance of the cured concrete. In some instances, entire batches of concrete must be destroyed or sold as cull product if the water content is not appropriately controlled.

Under current methods, water content of the mixture moving on the conveyor is estimated by random sampling on the run and by direct measurement of water in sand and aggregate stockpiles. Usually, such measurements are made once or twice a day and cannot estimate the variability of the water in the stock pile from surface drying during the day and/or rainfall that may occur. Such measurements also take a longer time, usually requiring about half an hour or more. Typically, the operator takes a select amount from the stock pile, weighs the amount, dries it on an electric or gas stove top and finds the mass lost to evaporation. The mass lost is determined as a gravimetrical percent moisture based on dry or wet mass of initial total aggregate.

In another method widely used in industry for determining water content, a probe is directly buried in sand or sand and aggregate within bins and/or hoppers. The material may be held stationary or may flow out of the bin past the probe or hopper to a conveyor belt. The method relies on the correlation of the dielectric properties of the water content of the material. The probe measures the dielectric properties of the material, and, based on a calibration, the water content of the material is determined. This method has limited accuracy in estimating the bulk water content of the material due to following draw backs: 1) when the material is stationary, the measurement volume of the probe is small compared to the majority of the material volume, resulting in an inaccurate detection of water in the bulk volume of the sample and 2) when material is flowing past the probe, the flow characteristics such as random air pockets, density variations, and turbulent material flow significantly increase the variance, reducing the average values, and leading to inaccurate water content data.

Nuclear and non-nuclear methods have been used to measure water content of construction materials for more than five decades. One such method described in U.S. Pat. No. 3,213,280 incorporates a neutron source and a slow neutron detector that utilized the fast neutron thermalizing effect or slowing down effect of hydrogen to measure water content in sand. The method described there was to measure the water content of sand used for molds and cores. The neutron source and the detector were placed inside a cylindrical probe. In calibration, the probe was buried in a container of carefully measured dimensions filled with sand so that the measurement volume of the probe covers most of the volume of sand in the container. Although this method is good for that particular application, the measurement volume is still a small fraction of the volume of bins and hoppers used in concrete plants. Chemical composition errors remained in the systems as well as density errors associated with moisture values.

Methods that determine water content of a concrete mixture when the mixture is moving on a conveyor belt have the advantage of estimating water content of a large integral fraction of the mixture. When the mixture has water distributed non-uniformly, water content estimate for the bulk volume has better accuracy with "on the run" averaging. Furthermore, due to the nature of concrete plant operation, at a given measurement position or location, height, mass, and density of the mixture moving on the belt varies with time. When determining the water content, methods should be used to compensate for such variations.

To compensate moisture measurements for the variation in height and mass of the mixture moving on the belt with time, one practice may be to use two or more independent methods for determining the height or mass thickness, and a quantity related to the water content of the mixture. Thereafter, physical relationships between the height or mass thickness, and a quantity related to water content are used to estimate or obtain direct measurements of the water content of mixture.

In nuclear techniques based on this proposed method, gamma-ray techniques are used to measure height or mass thickness and neutron techniques are used to measure a quantity related to water content of the mixture. Such methods are described in a report by Muller, R. H. (1963), Anal. Chem., Vol. 35(1), pp 99A-101A, and U.S. Pat. Nos. 3,255,975, 3,431,415, 3,748,473, 3,955,087, 4,362,939, and 4,884,288. Problems with the previous such methods is that they use nuclear radiation sources of large strength or activity, may have mechanical constraints to keep the mixture passing near the gauge at a constant height, and use specialized nuclear radiation detectors and sources, and complex electronic circuitry that were problematic for plant maintenance. Furthermore, error corrections on the fly associated with chemical composition, real-time corrections to flow discontinuities associated with random material height, thickness, density, and mass thickness, linked to belt speed and separation of detectors, are not fully described in previous art.

A need therefore exists for a method or solution that addresses these disadvantages and provides a real-time assessment of the concrete mixture. This solution can produce real time or near real time data, averaged, integral, and filtered results instantaneously.

SUMMARY

This Summary is provided to introduce a selection of concepts in a simplified form that are further described below in the Detailed Description of Illustrative Embodiments. This Summary is not intended to identify key features or essential features of the claimed subject matter, nor is it intended to be used to limit the scope of the claimed subject matter.

Disclosed herein is a system for use with a construction material. The system may include a conveyor apparatus configured for conveying a material. A water content detector is positioned about the conveyor apparatus for detecting moisture in the material and a dimension or quantity characteristic detector for detecting one or more dimension characteristics of the material. A computer device is configured to manipulate data received from the water content detector and the dimension characteristic detector to determine a corrected water content of the material. Quantity characteristic may mean a thickness (m), mass (kg), volume ($m^3$), mass thickness (kg-m), area ($m^2$), density ($kg/m^3$), linear length (m), mass per length (kg/m), mass per area ($kg/m^2$), time (s), speed (m/s), conveyor rate (1/s) and various combinations of the units or other dimensional characteristics. Mass thickness may be defined as a ratio such as mass per meter or mass per square meter. Water content may be relative, volumetric or gravimetric, based on wet or dry product, and/or converted from one set of units to another.

According to one or more embodiments, the water content detector and the dimension characteristic detector may be spaced-apart about the conveyor apparatus to eliminate relative cross-talk therebetween.

According to one or more embodiments, the water content detector includes a neutron source spaced-apart from one side of the conveyor apparatus and neutron detector spaced-apart from an opposing side of the conveyor.

According to one or more embodiments, the neutron source is Cf-252 and the neutron detector is an He-3 neutron or other detector.

According to one or more embodiments, the dimension characteristic detector is configured to determine one of a height or mass thickness of the material. A gravimetric or volumetric determination may be made.

According to one or more embodiments, the dimension characteristic detector includes a gamma-ray source spaced-apart from one side of the conveyor apparatus and a gamma-ray detector spaced-apart from an opposing side of the conveyor apparatus. Back scatter may also be employed.

According to one or more embodiments, the gamma-ray source is Cs-137 and the gamma-ray detector is a scintillation detector.

According to one or more embodiments, the water content detector is positioned downstream of the dimension detector.

According to one or more embodiments, the material is one of a concrete, bituminous mixture, sand, aggregate, concrete additives, water or a combination thereof.

According to one or more embodiments, the dimension characteristic detector uses one of acoustics, ultrasonic, structured light, lasers, optical, and combinations thereof for determining one of more dimension characteristics. A gravimetric or volumetric determination may be made.

According to one or more embodiments, the computer device is further configured to determine whether the water content characteristic is within an acceptable range and provide adjustments to water input of the material based on the determination.

According to one or more embodiments, a method for determining the water content of a material being transported on a conveyor apparatus is provided. The method includes detecting water content in the material, detecting a dimension characteristic of the material, and determining a water content of the material based on the detected water content and detected dimension of the material.

According to one or more embodiments, detecting water content in the material includes counting neutrons on one side of the conveyor apparatus emitted from a neutron source from an opposing side of the conveyor apparatus.

According to one or more embodiments, detecting a dimension characteristic of the material includes using one of acoustics, ultrasonic, structured light, lasers, optics, radar principles, and combinations thereof for determining one or more dimension characteristics.

According to one or more embodiments, detecting a dimension characteristic of the material includes counting gamma-rays (photons) on one side of the conveyor apparatus emitted from a gamma-ray source from an opposing side of the conveyor apparatus.

According to one or more embodiments, detecting a dimension characteristic of the material includes detecting one of a height or mass thickness of the material.

According to one or more embodiments, a density correction may occur.

According to one or more embodiments, a device for determining a characteristic of a construction material being transported by a conveyor apparatus is provided. The device includes one of a gamma-ray and a neutron source positioned about one or opposing sides of the conveyor apparatus and at least one detector positioned about the opposing side of the conveyor apparatus configured for detecting one of the gamma-ray and neutron source. A computer device is configured to manipulate data received from the detector to determine a characteristic of the construction material.

According to one or more embodiments, the detector is configured for detecting water content in the material.

According to one or more embodiments, the detector is configured for detecting a height, density, or a mass thickness of the material.

According to one or more embodiments, a mechanical device may be provided to scrape or otherwise form the material to a predetermined dimensional characteristic.

BRIEF DESCRIPTION OF THE DRAWINGS

The foregoing summary, as well as the following detailed description of preferred embodiments, is better understood when read in conjunction with the appended drawings. For the purposes of illustration, there is shown in the drawings exemplary embodiments; however, the presently disclosed invention is not limited to the specific methods and instrumentalities disclosed. In the drawings.

DETAILED DESCRIPTION

The presently disclosed invention is described with specificity to meet statutory requirements. However, the description itself is not intended to limit the scope of the one or more embodiments shown and described herein. Rather, the inventors have contemplated that the claimed invention might also be embodied in other ways, to include different steps or elements similar to the ones described in this document, in conjunction with other present or future technologies.

Figure 1:
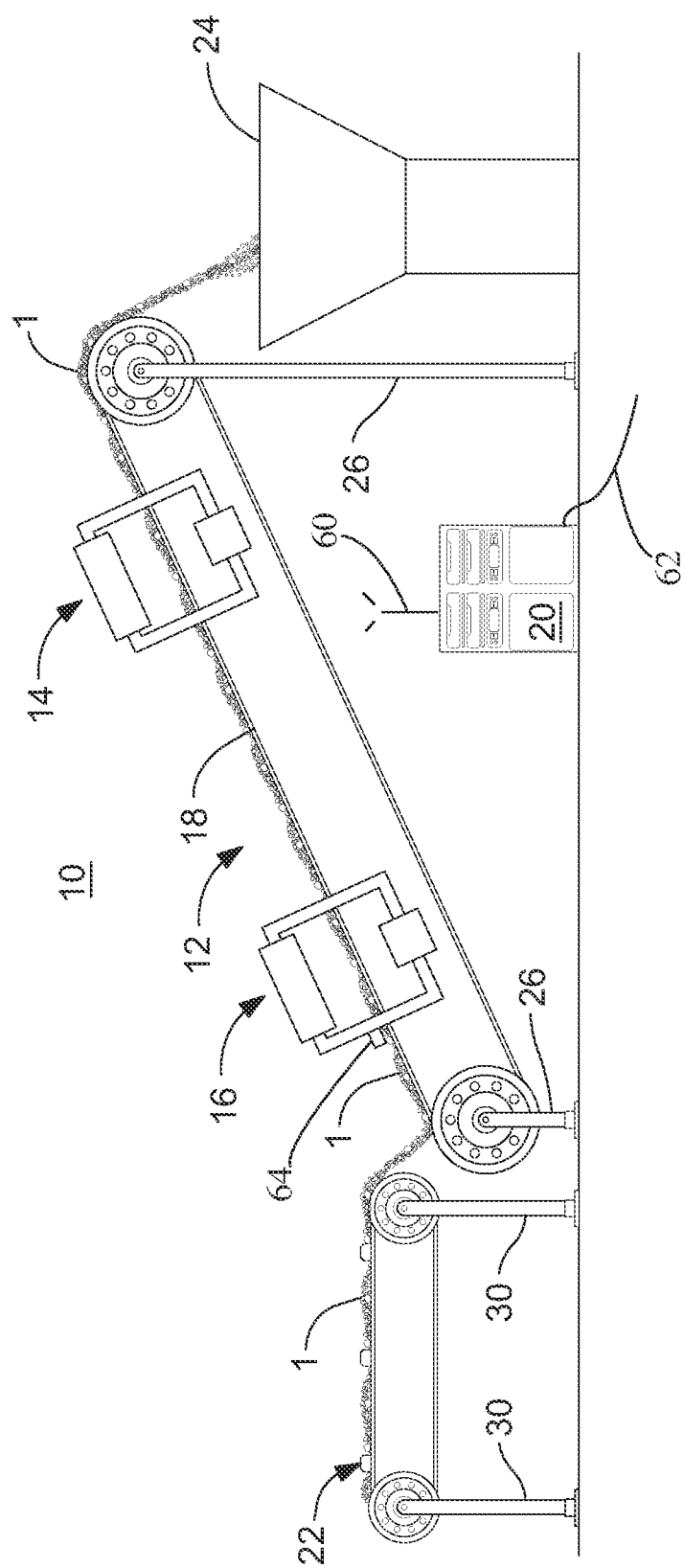
FIG. 1 is a side view of a conveyor system in accordance with one or more embodiments disclosed herein.

FIG. 1 illustrates a system 10 for processing concrete or other construction materials. The system 10 includes a conveyor apparatus 12 configured for conveying a material 1 about a conveyor track 18. The material 1 may contain any one of a concrete, bituminous mixture, sand, aggregate, concrete additives, water, air, or a combination thereof. In one or more embodiments, material 1 may also be coal or other ore based materials. The material flow in the conveyor apparatus 12 as illustrated is from left to right. A dimension characteristic measurement system 14 may be positioned about the conveyor apparatus 12 for detecting one or more dimension characteristics of the material 1. A water content measurement system 16 may be positioned about the conveyor apparatus 12 for detecting water content in the material. A material scraping device 64 may be provided about the water content measurement system 16 in order to remove excess amounts of material 1 before being interacted with by the water content measurement system 16. The speed of the web at the conveyor apparatus 12 may be monitored.

A computer device 20 is in communication with the water content measurement system 16 and dimension characteristic measurement system 14 and is configured to manipulate data received therefrom to determine a water content of the material 1. The water content may be a function of the detected water and the detected material dimensions. For example, a material having an otherwise increased thickness will thereby have an associated increase in detected neutrons, which may be read as an increased water content if the thickness of the material is not taken into consideration. The computer device 20 may be configured to normalize water content with the determined mass thickness. Communication with the computer device 20 may be wireless or hard wired, such as, for example, through the use of transmitter 60 or hardwire 62. The computer device 20 may be further configured to include one or more aspects of a global positioning system (GPS) for providing identification, mix properties, and location tracking services and information about the system 10 to either the on-site operator or a remote operator or to a customer. The conveyor 12 may be a mobile system or permanently placed at a plant.

The water content measurement system 16 may also be configured for detecting water or moisture by use of Boron-10 isotopes, coated gas tubes, BF3 filled gas tubes, lithium, solid state measures, and other detector types.

The conveyor apparatus 12 may be in further communication with an additional conveyor apparatus 22 and bin assembly 24. Bin assembly 24 could also be a homogenization tank for addition of water to the material 1. Additionally, moisture or water detection may occur in conveyor apparatus 22 or bin assembly 24. A frame member 26 may be provided for elevating the conveyor apparatus 12. Similarly, a frame member 30 may be provided for elevating additional conveyor apparatus 22.

The water measurement system 16 and the dimension characteristic measurement system 14 are illustrated in a spaced-apart arrangement about the conveyor apparatus 12 to eliminate cross-talk therebetween. In one or more embodiments, there may be about six (6) feet of spacing between the dimension characteristic measurement system 14 and the water content measurement system 16. Shields or additional structures may be employed for further limiting cross-talk between the dimension characteristic detector 14 and the water content detector 16 and may allow for more closely-spaced arrangement of the two measurement systems. Source and detector positions may be on opposing sides of the conveyor apparatus 12 or may be on the same side in a back scatter configuration.

Alternatively, the water content measurement system 16 may be configured for determining water content by using an electromagnetic source and detecting one or more characteristics such as impedance or scattering parameters. Exemplary techniques for use in determining a water property include using fringing field capacitors to produce an electromagnetic field; time domain reflectometry techniques; single-frequency moisture techniques; sweeping-frequency moisture techniques; microwave absorption techniques; radar reflection techniques; transmission techniques; and/or amplitude and microwave phase shift techniques. Further, suitable moisture signal detectors include detectors operable to measure the real and imaginary parts of a dielectric constant at a single frequency, multiple frequencies, continuous sweeps of frequencies, and/or chirps of frequency content, or involve time domain pulse analysis. An electromagnetic source may result in electromagnetic radiation or non-radiative fields in contact or not in contact with the material 1 or conveyor apparatus 12.

Figure 2:
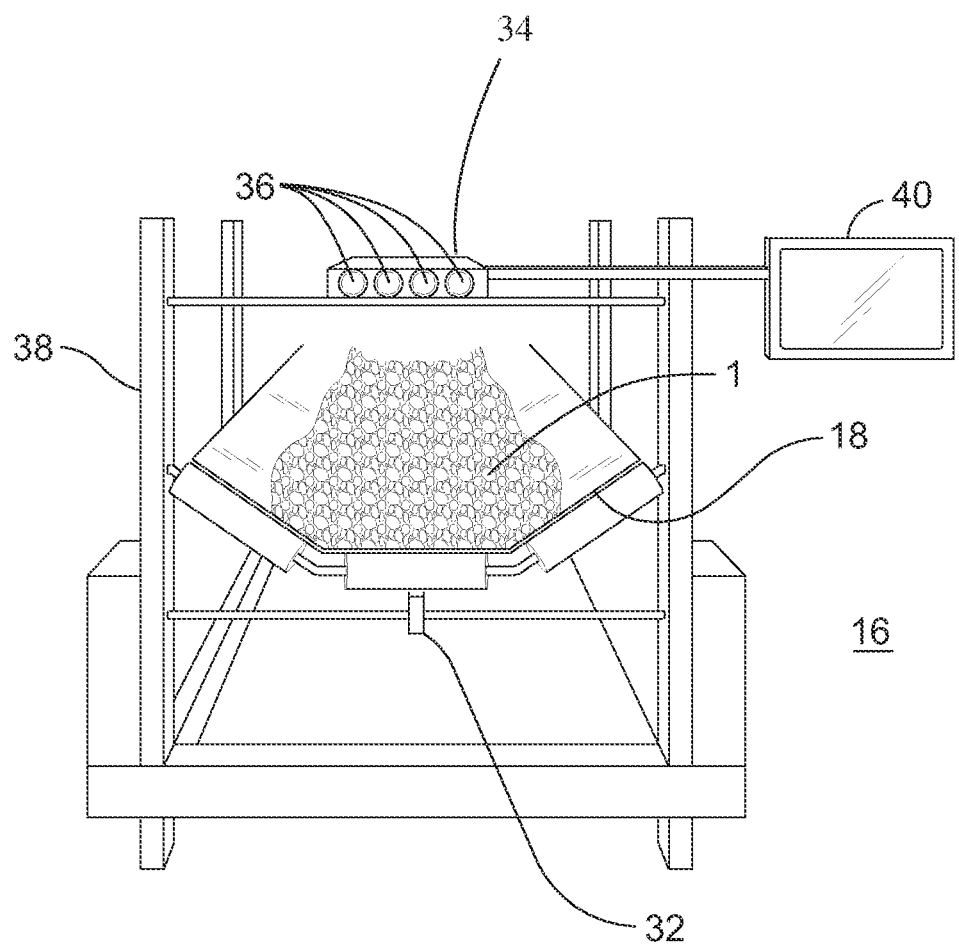
FIG. 2 is a front view of a water content detector for use with a conveyor system in accordance with one or more embodiments disclosed herein.

The water content measurement system 16 is illustrated more closely in FIG. 2. The water content measurement system 16 may include a neutron source 32 spaced-apart from one side of the conveyor track 18 and neutron detector 34 spaced-apart from an opposing side of the conveyor track 18. In this manner, neutron source 32 is configured for emitting neutrons into material 1 and the neutron detector 34 is configured for determining the counting statistics and/or energy state of neutrons passing through the material 1. In one or more embodiments, the neutron source 32 may be a 100 micro Curie source of Cf-252 having a half life of about 2.64 years. However, other suitable neutron sources may be employed, such as an Am-241/Be or any other suitable isotope/chemical or accelerator-based neutron sources for example. In one or more embodiments, a preferred configuration is transmission.

The neutron detector 34 may include one or more He-3 detectors 36 for detecting moderated neutrons. The He-3 detectors may include a gas tube with He-3. A frame 38 may be provided for supporting the neutron source 32 and the neutron detector 34. A display screen 40 may be communicatively coupled or remotely coupled visually interfacing the control operator to the water content measurement system 16 for displaying one or more measurements thereof. The water content measurement system 16 may be configured to provide a reading over a predetermined period of time. For example, the water content detector 16 may be configured to provide a reading of water content at specific times or at timed intervals. The water content measurement system 16 may be further configured to detect water over a predetermined number of occurrences, and the computer device 20 may be configured to average or filter the readings of the predetermined number of occurrences.

The neutron detector 34 may be operatively configured to detect moisture by determining the amount of hydrogen in material 1. Specifically, fast neutrons emitted by the neutron source 32 pass through the material 1 and undergo collisions with atomic nuclei in the material, thereby losing energy and slowing down. Hydrogen that is present within the water has a mass similar in magnitude to the neutron. Collisions of the neutrons with hydrogen atoms slow the neutrons down. By counting the number of slowed neutrons passing through, this may give an indicator as to the amount of hydrogen, and therefore water content present. However, the thickness of material 1 present on the conveyor track 18 can vary from measurement to measurement, so determining the amount of material 1 present may be necessary for converting the neutron count into a water content. Neutron count may be dependent on the density of the material 1 and the thickness of the material 1.

Figure 3:
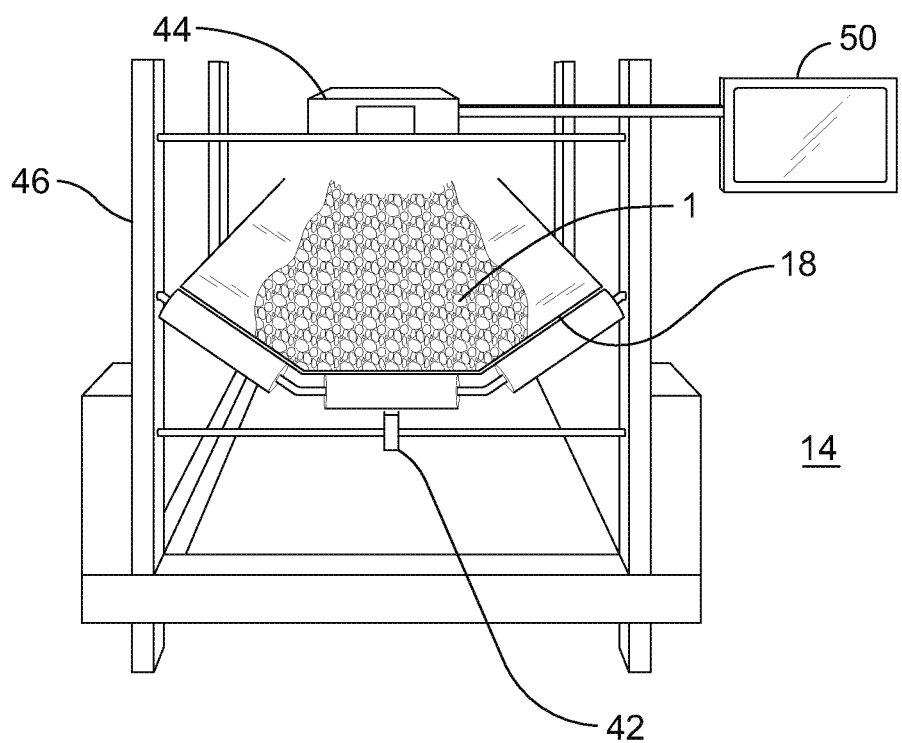
FIG. 3 is a front view of a dimension characteristic detector for use with a conveyor system in accordance with one or more embodiments disclosed herein.

The dimension characteristic measurement system 14 is illustrated more closely in FIG. 3. The dimension characteristic measurement system 14 may be configured to determine one of a height and mass thickness of the material 1. A volumetric and gravimetric determination may be made. The dimension characteristic measurement system 14 includes a gamma-ray source 42 spaced-apart from one side of the conveyor track 18 and a gamma-ray detector 44 spaced-apart from the opposing side of the conveyor track 18. The gamma-ray detector 44 may be configured for counting gamma rays (photons) of various energies, or counting gamma rays of any energy. In one or more embodiments, the gamma-ray source 42 is Cs-137 and may have a 300 micro Curie strength. However, other suitable gamma radiation sources with different primary energy levels may be employed, such as a Co-60, or any other suitable isotope gamma radiation source for example. In one or more embodiments, the gamma-ray detector 44 is a scintillation detector. In one or more embodiments, the scintillation detector may be an NaI or PMT detector. A frame 46 may be provided for carrying the gamma-ray source 42 and gamma-ray detector 44. A computer device having a display screen 50 may be communicatively coupled or remotely coupled to a central operator and the dimension characteristic measurement system 14 for displaying one or more measurements thereof. Alternatively, computer device 20 may be communicatively coupled to the water measurement system 16 and the dimension characteristic measurement system 14.

Additionally, in one or more embodiments, the dimension characteristic measurement system 14 may be configured to determine a dimension using one of acoustics, ultrasonic, structured light, lasers, optics, radar techniques, mechanical feelers, and combinations thereof methods.

The dimension characteristic measurement system 14 may be further configured for taking a first measurement at the beginning of a production run with an empty conveyor track 18. In this manner, the thickness of the conveyor track 18 and surrounding hydrogen can be measured and accounted for when determining a dimension of the material 1.

Figure 4:
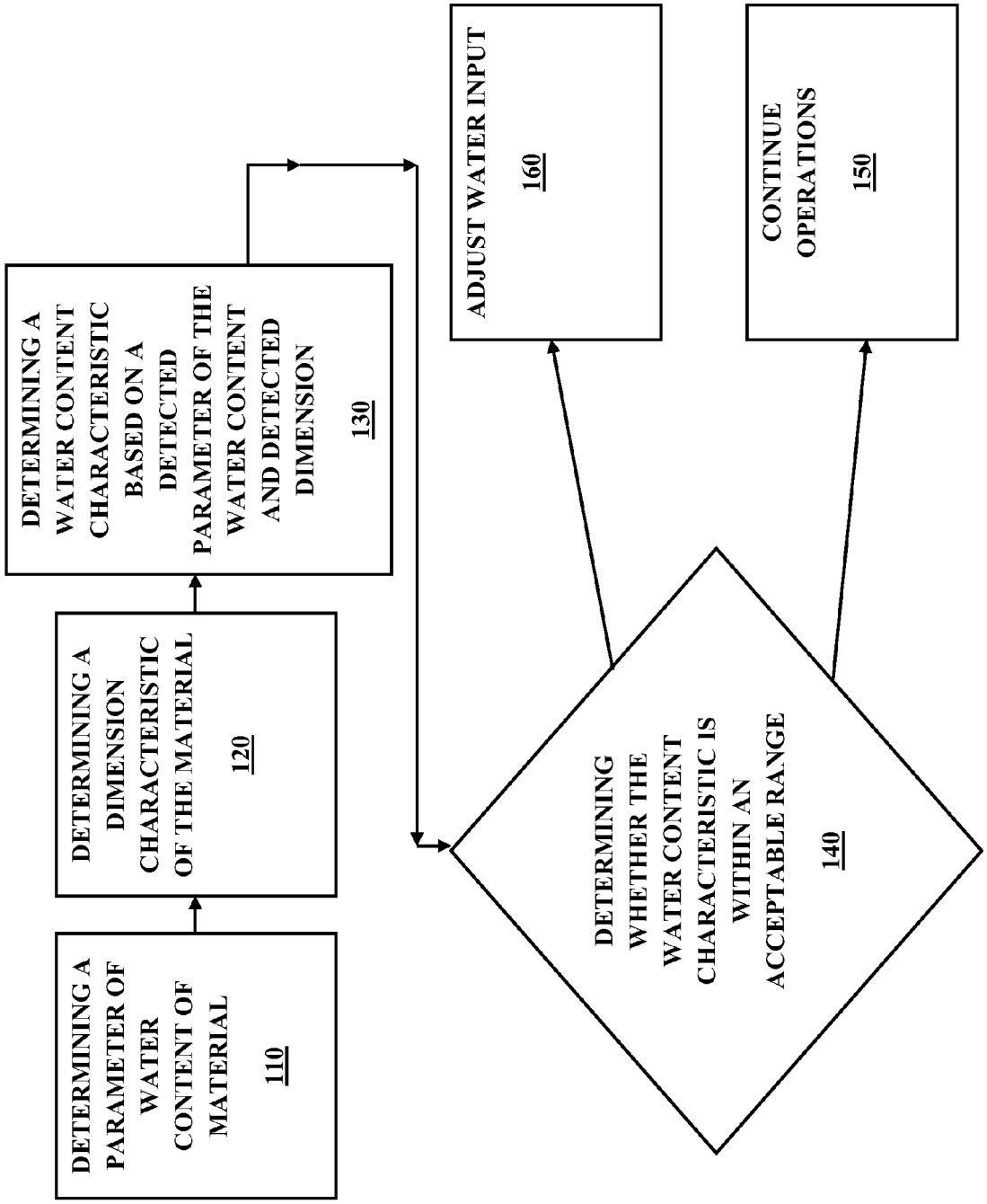
FIG. 4 is a flow chart of a method for determining a water characteristic of a material according to one or more embodiments disclosed herein.

One or more methods for determining a water content of a material being transported on a conveyor apparatus are illustrated in the flowchart of FIG. 4 and generally designated 100. The one or more methods 100 include determining a quantity or parameter of water related to water content in the material 110. Determining a quantity or parameter of water related to water content in the material 110 may include counting neutrons on one side of the conveyor apparatus emitted from a neutron source from an opposing side of the conveyor apparatus. Determining a quantity or parameter of water related to water content in the material 110 may be effectuated by utilization of the one or more water content measurement systems 16 disclosed herein.

The one or more methods 100 may include determining a dimension characteristic of the material 120. Determining a dimension characteristic of the material 120 may include using one of acoustics, ultrasonic, structured light, lasers, optics, radar, and combinations thereof for determining one or more dimension characteristics. Determining a dimension characteristic of the material 120 may include counting using a gamma-ray source and a scintillation detector. Determining a dimension characteristic 120 of the material may include detecting one of a height or mass thickness of the material. Determining a dimension characteristic of the material 120 may be effectuated by utilization of the one or more material dimension characteristic measurement systems 14 disclosed herein.

The one or more methods 100 may include determining a water content characteristic of the material based on the detected water parameter and detected dimension characteristic of the material 130. Determining a water content characteristic 130 may include using a computing module to analyze and determine the water characteristic based on the detected water parameter and dimensions of the material. The water characteristic may be, for example, a percentage of water or Hydrogen in the material 1 by weight, mass, or volume. A density may also be computed. In one or more embodiments, computer 20 may be configured to synchronize measurements of the dimension characteristic detector 14 and water content detector 16 based on the velocity of conveyor belt 18 so that respective measurements are being taken of the same portion of material 1. Detecting water content may use one or more normalizing variables, such as water content and density. Synchronizing measurements may also depend on material flow characteristics. For example, the speed and mass thickness of the material may be used to synchronize measurements of the dimension characteristic detector 14. A delay may be introduced between measurements based on the speed of the conveyor belt 18.

The one or more methods 100 may include determining whether the water content characteristic is within an acceptable or predetermined range 140. For example, if water content is supposed to be below 3.0% in a given material, the desired range may be predetermined to be between 2.5% and 3.0% water content. The computer device 20 may be configured for communicating with the water content measurement system 16 and dimension characteristic measurement system 14 for determining whether the detected water content characteristic is within the acceptable range.

If the water content characteristic is within an acceptable range, operation of the system 10 may continue with continuous monitoring of the material characteristics 150. If the water content characteristic is not within an acceptable range, the system 10 may adjust the water input 160 of the material. This may be accomplished instantaneously with the system 10 continuing to operate so that there is no down-time, or, alternatively, the system 10 can cease production while adjustments are made to water input. This adjustment to water input may be accomplished by addition of water, removal of water through pressing or other mechanical processes, thermal application, addition or removal of material, and combinations thereof.

The computer device 20 illustrated in FIG. 1 may include computer control code configured for carrying out the one or more methods 100 disclosed herein. For example, the computer control code may be configured for communicating with moisture 16 and dimensional 14 apparatus, instrumentation on the hopper 24 and conveyors 12 and 22, display screens 40 and 50 for outputting one or more data parameters. The computer control code may be configured for comparing the detected water content and the detected dimension characteristic to determine a water property of the material. Computer may be directly linked to a control room, hardware controller, or operator in a separate location.

Figure 5:
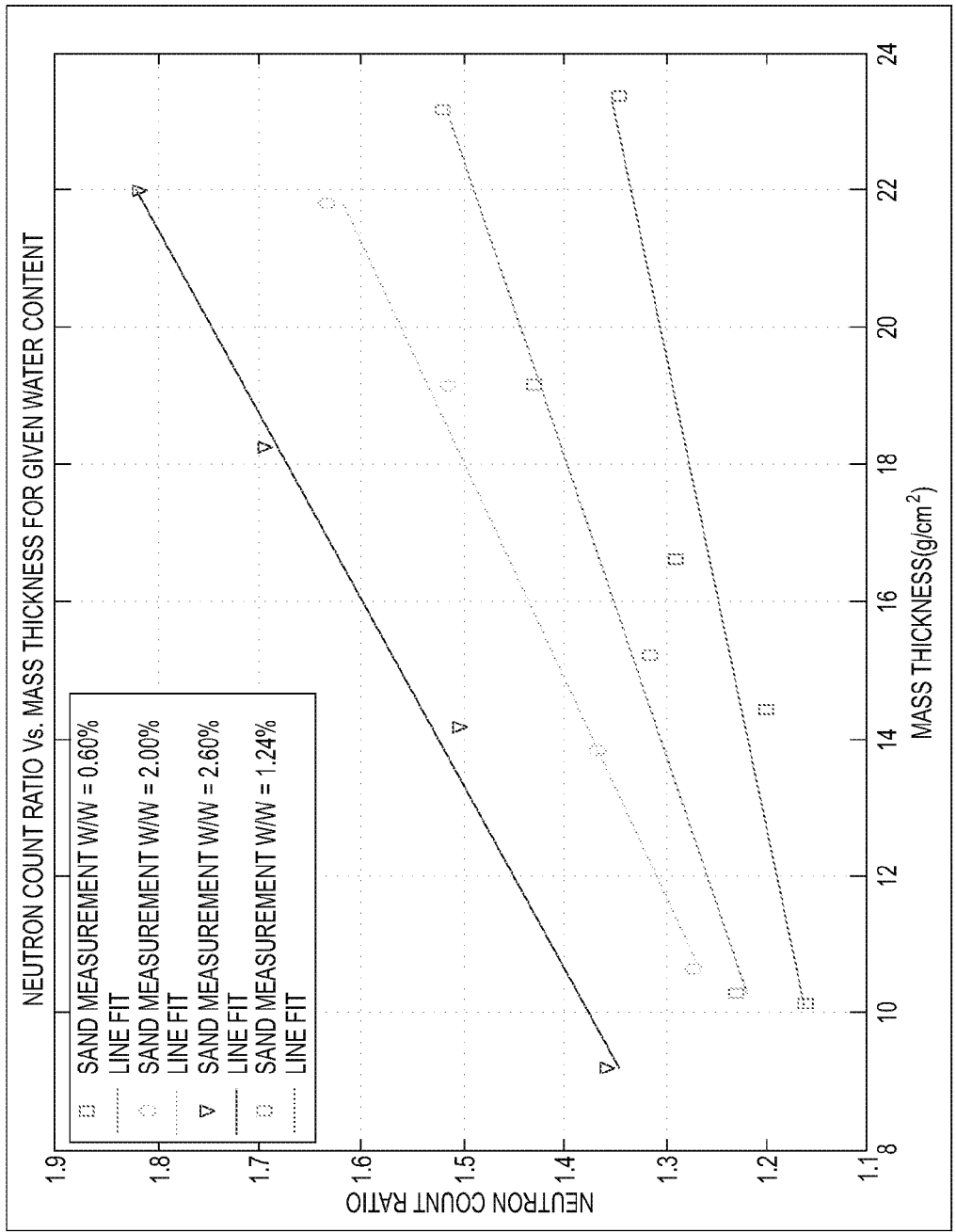
FIG. 5 is a chart showing experimental results for determining a water characteristic according to one or more embodiments disclosed herein.

The computer device 20 may be configured to provide an algorithm or other computer control code for displaying information such as the experimental results illustrated in the chart of FIG. 5. As illustrated in FIG. 5, the experimental results show a generally linear correlation between neutron count ratio and material thickness for a given control material having a known water content. Similar experimental results may be established showing a linear arrangement for concrete mixtures and by comparing the detecting water characteristic with the detected mass thickness, a water content of the material may be determined. The computer device 20 may be configured to provide a printout of various data and characteristics determined. The system 10 may further include global positioning system (GPS) capabilities.

The relationship between count ratio and material thickness or mass thickness may also be correlated to the speed of the additional conveyor and a known mass of the material as a function of time being applied to belt 22. Count ratio applies to either neutron or gamma system and refers the actual material measurement count as related to a standard count. Standard count may be a daily count using standard hydrogenous materials or dense materials such as Mg, Al, Mg—Al, Polypropylene or combinations of these materials. Standard count may simply be an empty belt count, or air count, at a particular position of the conveyor, or several points on the conveyor or an integral average of a running conveyor. Thus, FIG. 5 demonstrates a dynamic real time collaboration relationship between count ration and material thickness or mass thickness.

Figure 6:
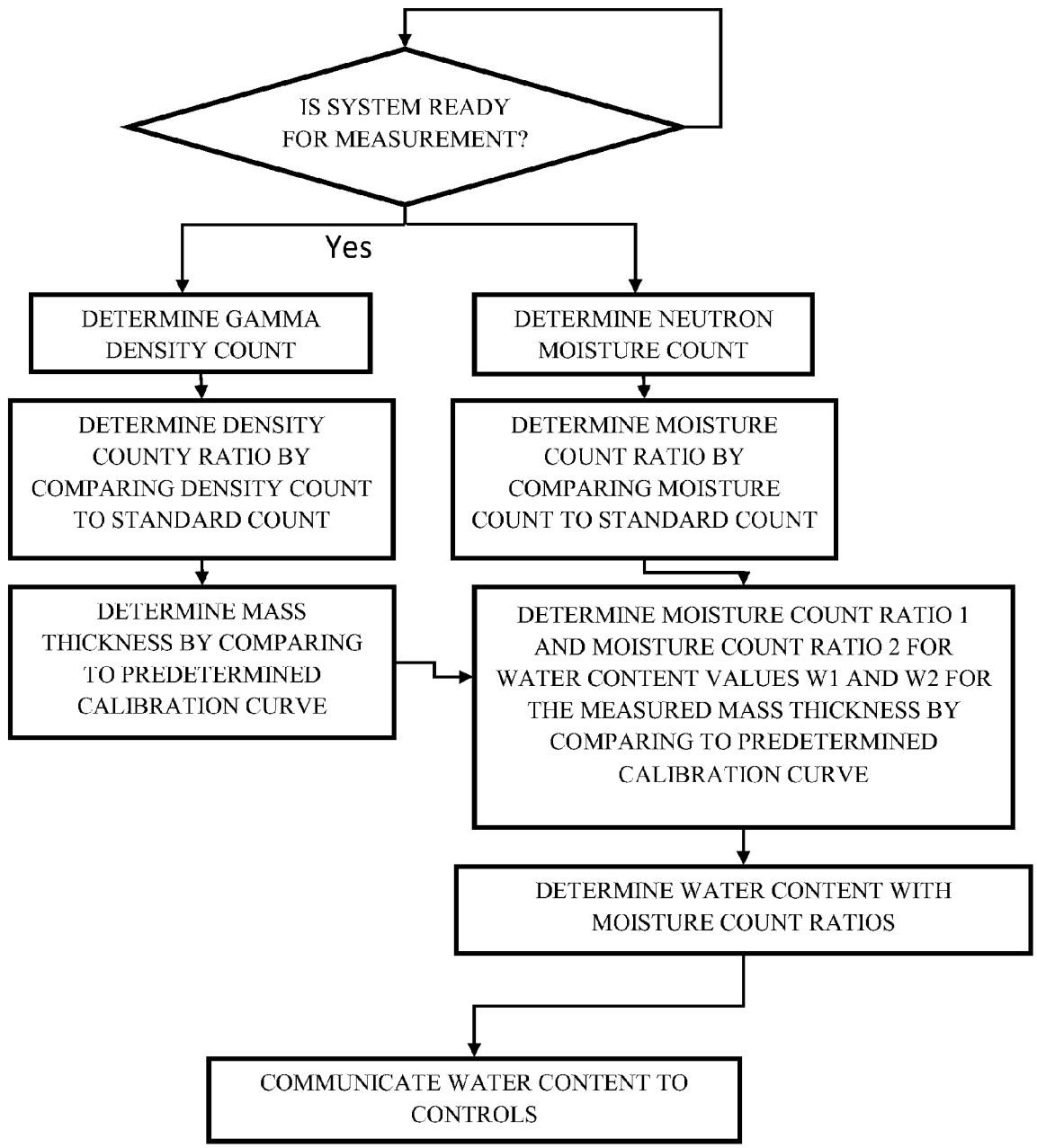
FIG. 6 is a flow chart of a method for determining a water content within a material and communicating that content to a computer device according to one or more embodiments disclosed herein.

FIG. 6 illustrates a method for determining water content and communicating the water content to the computer device. The system first determines if it is ready for measurement 210. If yes, then the system may, either simultaneously or at an offset time, determine a gamma density count of the material 212 and determine a neutron moisture count 220. This determination may be made over a predetermined interval, such as, for example, one second. The method may include determining a density country ratio by comparing the density count to a standard count 214, meaning a count when no material is on the conveyor. The method may include determining a moisture count ratio by comparing moisture count to a standard count 222. The density count ratio step 214 and moisture count ratio 222 may be performed simultaneously or at offset times thereof. The method may include determining mass thickness by comparing to a predetermined calibration curve 216. The method may then include determining a moisture count ratio 1 and a moisture count ratio 2 for water content values w1 and w2 by comparing the moisture count ratio and the calibration curve 224. The method may include determining a water content with the moisture count ratios 226. The method may include communicating the water content to a computer device 230. The method may include digital filtering the data or simple averaging or a video or running average technique.

While the embodiments have been described in connection with the preferred embodiments of the various figures, it is to be understood that other similar embodiments may be used or modifications and additions may be made to the described embodiment for performing the same function without deviating therefrom. Therefore, the disclosed embodiments should not be limited to any single embodiment, but rather should be construed in breadth and scope in accordance with the appended claims.

What is claimed:

1. A system comprising:
    a conveyor apparatus configured to convey a construction material;
    a neutron measurement system positioned about the conveyor apparatus and configured to determine a water content response in the construction material based on a dynamic real time calibration relationship;
    a dimension characteristic system configured to determine at least one dimension characteristic of the construction material, wherein one of the dimension characteristics of the construction material is a thickness related parameter; and
    a computer device configured to:
        receive the determined response and the at least one dimension characteristic of the construction material; and
        use the dynamic real time calibration relationship to select a relationship between neutron response and the thickness parameter to determine moisture content based on dimensional and neutron characteristics to determine a moisture content in the construction material.

2. The system according to claim 1, wherein the neutron measurement system and the dimension characteristic measurement system are spaced-apart about the conveyor apparatus to eliminate cross talk therebetween.

3. The system of claim 2, wherein moisture content is one of relative, volumetric, and gravimetric based on wet or dry products.

4. The system according to claim 1, wherein the neutron measurement system comprises a neutron source spaced-apart from one side of the conveyor apparatus and a neutron detector spaced-apart from an opposing side of the conveyor.

5. The system according to claim 4, wherein the neutron source is at least one of a Cf-252 and Am-241:Be and the neutron detector is at least one of an He-3 neutron detector, boron 10 isotopes, coated gas tubes, lithium detectors, solid state measures, and a BF3 neutron detector.

6. The system according to claim 1, wherein the dimension characteristic measurement system is configured to determine one of a height and mass thickness of the material.

7. The system of claim 6, wherein the dimension characteristic is one of thickness, mass, volume, mass thickness, area, density, linear length, mass per length, mass per area, time, and speed conveyor rate.

8. The system according to claim 1, wherein the dimension characteristic system comprises a gamma-ray source spaced-apart from one side of the conveyor apparatus and a gamma-ray detector spaced-apart from an opposing side of the conveyor apparatus and is configured for detecting a mass thickness.

9. The system according to claim 8, wherein the gamma-ray source is Cs-137 and the gamma-ray detector is a scintillation detector.

10. The system according to claim 1, wherein the neutron measurement system is positioned one of upstream and downstream of the dimension characteristic system.

11. The system according to claim 1, wherein the construction material is one of a concrete, bituminous mixture, coal based, ore based, sand, aggregate, concrete additives, water or a combination thereof.

12. The system according to claim 1, wherein the dimension characteristic system uses one of acoustics, ultrasonic, structured light, lasers, optics, radar, gamma ray, mechanical feelers, and combinations thereof methods for determining one of more dimension characteristics.

13. The system according to claim 1, wherein the computer device is further configured to:
    determine whether the water content is within an acceptable range; and
    provide a water adjustment amount or correction factor for the water input for the construction material based on the determination.

14. The system according to claim 1, further comprising a moisture system is further configured to use one of thermal neutrons, microwaves, radar, optics and combinations thereof methods for determining one or more water characteristics.

15. The system according to claim 1, further comprising a moisture system is further configured to determine a total hydrogen characteristic in combination with one of thermal neutrons, microwaves, radar, optics and combinations thereof methods for determining one or more water and hydrogen characteristics.

16. The system of claim 1, wherein the computer device is configured to determine a corrected water content of the material.

17. The system of claim 1, wherein the real time corrections to flow discontinuities associated with at least one of belt speed, detector placement, random material height, mass thickness, and density are dynamically determined in real time and used to measure moisture or asphalt content.

18. A method for determining moisture content in a construction material being transported on a conveyor apparatus, the method comprising:
using a neutron measurement system to determine an amount of water content in the construction material based on a dynamic real time calibration relationship;
determining at least one dimension characteristic of the construction material, wherein one of the dimension characteristics of the construction material is a thickness related parameter;
receiving the determined amount and the at least one dimension characteristic of the construction material; and
using the dynamic real time calibration relationship to select a relationship between neutron response and the thickness parameter to determine moisture content based on dimensional and neutron characteristics to determine a moisture content in the construction material.

19. The method according to claim 18, wherein using a neutron measurement system comprises using the neutron measurement system to determine the neutron response on one side of the conveyor apparatus emitted from a neutron source from an opposing side of the conveyor apparatus.

20. The method according to claim 18, wherein determining at least one dimension characteristic of the construction material comprises using one of acoustics, ultrasonic, structured light, lasers, optics, radar, mechanical feelers, gamma ray, and combinations thereof for determining one or more dimension characteristics.

21. The method according to claim 18, wherein determining at least one dimension characteristic of the construction material comprises a gamma-ray response (photons) using a gamma-rays source and a scintillation detector.

22. The method according to claim 18, wherein determining at least one dimension characteristic of the construction material comprises determining one of a height or mass thickness of the construction material.

23. The method according to claim 18, wherein the construction material is one of a concrete, bituminous mixture, sand, coal based, ore based, aggregate, concrete additives, water or a combination thereof.

24. The method according to claim 18, further comprising:
determining whether the water content is within an acceptable range; and
providing a water adjustment amount or correction factor for the water input for the construction material based on the determination.

25. A device for determining a characteristic of a construction material being transported by a conveyor apparatus, the device comprising:
one of a gamma-ray and a neutron source positioned about one side of the conveyor apparatus;
a detector positioned about the opposing side of the conveyor apparatus configured for detecting one of the gamma-rays and neutrons; and
a computer device configured to:
receive a detected gamma-ray reading and a detected neutron reading;
manipulate the received detected gamma-ray reading and the detected neutron reading from the detectors to determine an amount of water content in the construction material and at least one dimension characteristic of the construction material, wherein one of the dimension characteristics of the construction material is a thickness related parameter; and
dynamically determine, in real time, a moisture content in the construction material based on the manipulated detected gamma-ray reading and the detected neutron reading.

26. The device according to claim 25, wherein the construction material is one of a concrete, bituminous mixture, sand, aggregate, coal based, ore based, concrete additives, water or a combination thereof.

* * * * *